(12) United States Patent
Dervyn

(10) Patent No.: US 10,892,893 B2
(45) Date of Patent: Jan. 12, 2021

(54) METHOD AND SYSTEM FOR KEY DISTRIBUTION BETWEEN A SERVER AND A MEDICAL DEVICE

(71) Applicant: Fresenius Vial SAS, Brézins (FR)

(72) Inventor: Olivier Dervyn, Tullins Isère/R.A. (FR)

(73) Assignee: Fresenius Vial SAS, Brézins (FR)

( * ) Notice: Subject to any disclaimer, the term of this patent is extended or adjusted under 35 U.S.C. 154(b) by 52 days.

(21) Appl. No.: 16/061,071

(22) PCT Filed: Nov. 9, 2016

(86) PCT No.: PCT/EP2016/077133
§ 371 (c)(1),
(2) Date: Jun. 11, 2018

(87) PCT Pub. No.: WO2017/102183
PCT Pub. Date: Jun. 22, 2017

(65) Prior Publication Data
US 2018/0359085 A1 Dec. 13, 2018

(30) Foreign Application Priority Data

Dec. 17, 2015 (EP) ..................................... 15307034

(51) Int. Cl.
*H04L 9/08* (2006.01)
*G16H 40/40* (2018.01)
(Continued)

(52) U.S. Cl.
CPC ........... *H04L 9/0827* (2013.01); *G16H 20/17* (2018.01); *G16H 40/40* (2018.01); *G16H 40/67* (2018.01);
(Continued)

(58) Field of Classification Search
CPC ....... H04L 63/062; H04L 9/08; H04L 9/0819; H04L 9/0822; H04L 9/083; H04L 9/0894;
(Continued)

(56) References Cited

U.S. PATENT DOCUMENTS

2004/0098581 A1   5/2004  Balfanz et al.
2004/0260363 A1*  12/2004 Arx .................... A61N 1/37252
                                                                607/60
(Continued)

FOREIGN PATENT DOCUMENTS

CN    101977543    2/2011
CN    102831294    12/2012
(Continued)

OTHER PUBLICATIONS

International Search Report and Written Opinion, counterpart International Appl. No. PCT/EP2016/077133, dated Dec. 8, 2016 (11 pages).
(Continued)

*Primary Examiner* — Trong H Nguyen
(74) *Attorney, Agent, or Firm* — Cook Alex Ltd.

(57) ABSTRACT

A method for key distribution between a server (1) and a medical device (3A, 3B), in particular an infusion device, comprises: providing, at the server (1), a security key (4A, 4B) to be used for a secure data communication of the medical device (3A, 3B); establishing a first communication link (11) between the server (1) and a computing device (2); establishing a second communication link (30A, 30B) between the computing device (2) and the medical device (3A, 3B); retrieving, by the computing device (2), the security key (4A, 4B) from the server (1) via the first communication link (11); and transmitting, by the computing device (2), the retrieved security key (4A, 4B) to the medical device (3A, 3B) via the second communication link (Continued)

Figure 1:
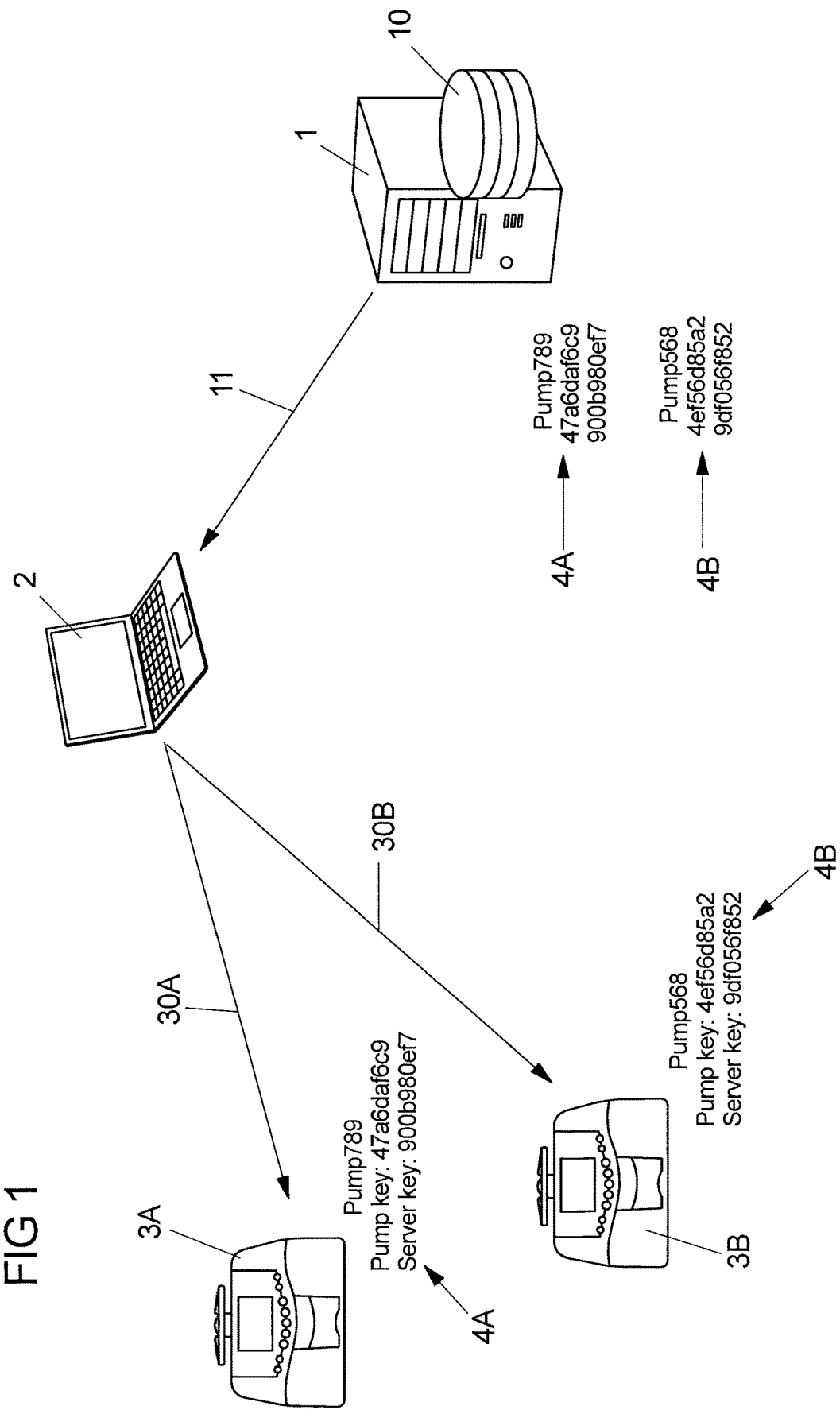

(30A, 30B). In this way a method for the security key distribution between a server and a medical device is provided, the method being suitable even for medical devices having low computational and memory capabilities.

12 Claims, 2 Drawing Sheets

(51) Int. Cl.
*H04L 29/06* (2006.01)
*G16H 40/67* (2018.01)
*G16H 20/17* (2018.01)

(52) U.S. Cl.
CPC ............ *H04L 63/062* (2013.01); *H04L 63/18* (2013.01); *H04L 9/0861* (2013.01)

(58) Field of Classification Search
CPC ..... H04L 9/0897; H04L 9/0827; H04L 63/18; H04L 2209/88; H05H 2277/10; G16H 20/17
See application file for complete search history.

(56) References Cited

U.S. PATENT DOCUMENTS

| | | | |
|---|---|---|---|
| 2005/0204134 A1* | 9/2005 | Von Arx | A61B 5/0031 713/168 |
| 2006/0218397 A1 | 9/2006 | Brown et al. | |
| 2007/0118397 A1* | 5/2007 | Williams | G06Q 50/22 705/2 |
| 2009/0157622 A1 | 6/2009 | Roberts et al. | |
| 2010/0292556 A1* | 11/2010 | Golden | A61B 5/7465 600/364 |
| 2011/0022411 A1 | 1/2011 | Hjelm et al. | |
| 2011/0179405 A1* | 7/2011 | Dicks | G06F 8/61 717/168 |
| 2014/0263616 A1 | 9/2014 | Zhuang | |

FOREIGN PATENT DOCUMENTS

| | | |
|---|---|---|
| CN | 104520855 | 4/2015 |
| WO | WO2011/002905 | 1/2011 |
| WO | WO2014/012475 | 1/2014 |

OTHER PUBLICATIONS

Search Report, counterpart Chinese App. No. 201680073064 (dated Jul. 27, 2020) (2 pages).
First Office Action with English translation, counterpart Chinese App. No. 201680073064 (dated Aug. 4, 2020) (19 pages).

* cited by examiner

HTTP message with signature
Ex: GET: http://www.MyServer.com/AgiliaV2/ID/789/AlarmStatus
?user=Pump789&timestamp=1356444113&12d885fd488ea565ba522cee8785dff Example HTTP message:
GET: http://www.MyServer.com/AgiliaV2/ID/789/AlarmStatus?user=Pump789&timestamp=1356444113 converted to Encrypted message:
145d..2d..88..fd..48..8e..a5..ba..52..2c..ee85

METHOD AND SYSTEM FOR KEY DISTRIBUTION BETWEEN A SERVER AND A MEDICAL DEVICE

The present application is a U.S. National Stage of PCT international Patent Application No. PCT/EP2016/077133, filed Nov. 9, 2016, which claims priority to EP Application No, 15307034, filed Dec. 17, 2015, both of which are hereby incorporated herein by reference.

The invention relates to a method and a system for key distribution between a server and a medical device.

The medical device may in particular be an infusion device, such as a volumetric or syringe infusion pump located for example on a rack at the bedside of a patient. The server and the medical device may for example be located within a hospital environment and may be configured to communicate with each other via a communication network, for example making use of the Internet Protocol (IP).

During setup or during operation of the medical device, for example the infusion device, messages are exchanged between the server and the medical device. These messages may comprise operational data as well as configuration data, which shall be protected from an access from the outside and from a manipulation by a non-authenticated third-party.

For the protection of data, typically, encryption technologies are used making use of complex cryptographic (and power consuming) algorithms (such as HTTPS). Medical devices, such as infusion pumps, due to limited CPU and memory capabilities however may not have the necessary computational power to use such complex encryption algorithms such that a security key distribution between a server and a medical device such as an infusion pump requires a different solution.

Commonly, symmetric-key algorithms and asymmetric-key algorithms are known and used for the encryption.

Symmetric-key algorithms use the same cryptographic keys for both encryption of plaintext and decryption of ciphertext. The keys may be identical, or there may be a simple transformation to go between the two keys. In practice the key is called a "shared secret" between two or more parties. The main drawback of symmetric key encryption is the key distribution vulnerability. If anybody has access to the secret key (and algorithm to cipher data), he has access to the secret data.

Asymmetric-key algorithms (public-key cryptography) refer to a set of cryptographic algorithms based on non-reversible mathematical properties. Asymmetric-key algorithms, unlike symmetric-key algorithms, do not require a secure channel for the initial exchange of one (or more) secret keys between the parties. Asymmetric-key algorithms are fundamental security ingredients in security applications and protocols (for example Transport Layer Security (TLS) or PGP).

It is an object of the invention to provide a method and a system for the security key distribution between a server and a medical device, the method in the system being suitable even for medical devices having low computational and memory capabilities.

This object is achieved by means of a method according to the features of claim 1.

Accordingly, the method comprises the steps of:
providing, at the server, a security key to be used for secure data communication of the medical device,
establishing a first communication link between the server and a computing device,
establishing a second communication link between the computing device and the medical device,
retrieving, by the computing device, the security key from the server via the first communication link, and
transmitting, by the computing device, the retrieved security key to the medical device via the second communication link.

The invention addresses security key management and broadcast for medical devices such as infusion pumps. The invention enables to distribute and manage security keys between a server and a medical device for a secure communication between the server and the medical device. By means of the security key distribution an encrypted communication as well as an authentication between the medical device and the server becomes possible.

A solution hence is proposed to solve confidentiality, integrity and authentication of both parts during security key distribution. Key distribution is a method to distribute cryptographic keys between two (or more) parties, allowing use of a cryptographic algorithm. A fundamental problem of key distribution is how to exchange keys (or other needed information) such that no one else can obtain a copy. The invention proposes a solution to get advantage of public key cipher algorithms (high level of security) to distribute keys and to get advantage of private key cipher algorithms (simplicity and low computing cost) to encrypt or decrypt messages.

One or multiple security keys may be distributed from the server to one or multiple medical devices such as infusion pumps. In particular, a key pair may be distributed from the server to a particular medical device in order to allow for an authentication and for an encrypted communication between the server and the medical device.

In another embodiment, a security key for example for a WiFi connectivity of the medical device may be distributed from the server to the medical device, for example a WPA2 password or a Radius Certificate.

The computing device may for example be a personal computer (PC) such as a laptop computer. The computing device however may also be a mobile device such as a mobile phone, a tablet computer or another mobile communication device having sufficient computational capabilities.

The first communication link via which the server is connected to the computing device may for example be a link making use of the Internet protocol. The link may for example make use of an HTTPS session and hence is protected by means of cryptographic algorithms implemented in HTTPS. The computing device hence communicates with the server via a preferably secured communication link such that the security key may be sent from the server to the computing device via a secured link, in particular in the context of an HTTPS session.

The second communication link between the computing device and the medical device may in particular be a wired link, such as a serial link (for example a RS232 link). The computing device hence locally is connected to the medical device via a dedicated communication line such that no particular and computationally expensive security algorithms are required to protect a communication between the computing device and the medical device.

The security key is provided at the server and is sent, via the first communication link, from the server to the computing device. The computing device may have sufficient computational power such that complex, high level cryptographic algorithms, for example in the context of an HTTPS session, may be used to protect the communication between the server and the computing device when transmitting the security key from the server to the computing device.

The computing device then sends the security key received from the server on to the medical device via the second communication link, wherein for this no encryption is necessary if a local link such as a wired link, in particular a serial link, is established between the computing device and the medical device. Hence, the medical device does not require extensive computational power, because complex cryptographic algorithms are not necessary to protect the communication between the computing device and the medical device.

In one embodiment, the computing device uses a dedicated software denoted as security application for distributing the security key from the server to the medical device. The dedicated software of the security application in particular establishes the communication with the server and makes sure that the security key received from the server is not stored by the computing device, but is only sent on to the medical device and is subsequently deleted at the computing device.

The medical device, for example the infusion pump, is constituted such that the security key cannot be read when accessing the medical device.

In one embodiment, a key pair comprising a server key and a device key is provided by the server, is retrieved from the computing device and is sent by the computing device to the medical device. Herein, the server may generate a multiplicity of different, dedicated key pairs associated with a multiplicity of medical devices, for example different infusion devices. Each medical device hence is associated with a dedicated key pair having a specific server key and a specific device key, the server keys and device keys used by the different medical devices being different from each other.

For example, medical device A may have server key A and device key A, whereas medical device B may have server key B and device key B. The key pairs of the different medical devices hence are distinct from each other For each medical device the key pair may be retrieved from the server by the computing device and may be transmitted to the particular medical device. Via the computing device the different key pairs hence are distributed to the different medical devices.

Once the key pairs are distributed to the different medical devices, a secure communication may take place between a medical device and the server, for example during operation of the medical device, such as an infusion pump, to provide operational data to the server. The communication link between the medical device and the server may for example make use of standard communication protocols, for example HTTP or any other kind of protocol (IP and non IP Protocol), wherein the key pair associated with a particular medical device may be used to authenticate the medical device at the server as well as to encrypt messages sent between the medical device and the server.

For example, for less critical data the medical device may send a clear message to the server within an HTTP session, the message having a signature generated according to at least one of the device key and the server key of the key pair associated with the medical device. The signature can be read by the server, and by means of the signature the server can authenticate the medical device such that it is ensured that the message is received from a trusted medical device and has not been manipulated by a third-party. In particular, if the method would be manipulated on its way from the medical device to the server, the signature would be changed, which could be detected by the server. If the server receives and detects a correct signature, the server knows that the message has not been manipulated and has been sent by an authenticated medical device.

To avoid message replay from a non-trusted third-party, each message may have a non-static part (for example date and time) to be sure to obtain a different signature computation for each message (because the same message with the same key may otherwise provide the same signature). For this, a time stamp or a counter may be added in the message body, and the server and/or the medical device may be configured to reject a message with a bad time stamp (i.e., a time stamp which is too old) or with a bad message counter. For these reasons, a time synchronization between each item of the system (medical device, server and computing device) may be initially performed.

In another example, the communication between the medical device and server may be encrypted, in particular for data that is to be protected. For encryption, at least one of the device key and the server key of the key pair may be used, wherein the medical device encrypts the message according to the key pair, and the server decrypts the message received from the medical device making use of the key pair, and vice versa. Again, to avoid a message replay from a non-trusted third-party, each message may have a non-static part (for example date and time) to be sure to obtain a different encryption for each message (because the same message with the same key may otherwise provide the same encryption).

It may be desirable to change a security key associated with a medical device after some time of usage, for example after sending a predefined amount of messages between the server and the medical device. A change of the security key may be requested by the medical device by sending an encrypted message to the server, upon which the server sends the new security key, for example a new key pair, in an encrypted message to the medical device. The message in which the new security key is sent to the medical device herein is encrypted making use of the old security key, for example the old key pair. Upon receiving the new security key, for example the new key pair, at the medical device, for the further communication between the medical device and the server then the new security key is used.

A specific change key message could be sent to the server to advise it of a key change. In this case, the message is encrypted with the old keys.

The object is also achieved by a system for key distribution between a server and a medical device, in particular an infusion device, the system comprising:
- a server configured to provide a security key to be used for a secure data communication of the medical device,
- a computing device, wherein the server and the computing device are configured to establish a first communication link between the server and the computing device,
- a medical device, wherein the computing device and medical device are configured to establish a second communication link between the computing device and the medical device.

Herein, the computing device is configured to retrieve the security key from the server via the first communication link and to transmit the retrieved security key to the medical device via the second communication link.

The advantages and advantageous embodiments described above for the method equally apply also to the system, such that it shall be referred to the above.

Figure 2:
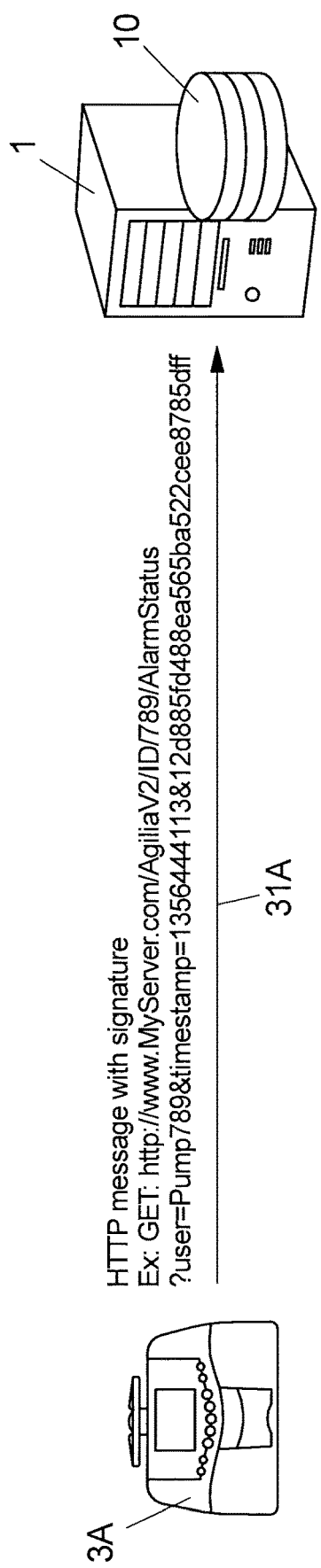
Figure 3:

The idea underlying the invention shall subsequently be described in more detail with regard to the embodiments shown in the figures. Herein, FIG. 1 shows a system comprising a server, a computing device and a multiplicity of medical devices;

FIG. 2 shows a communication between a medical device and the server using a message comprising a signature for authentication; and FIG. 3 shows a communication between a medical device and the server using an encrypted message.

FIG. 1 shows a system comprising a server 1, a computing device 2 such as a portable laptop computer and a multiplicity of medical devices 3A, 3B in the shape of infusion pumps. The system may be located in a hospital environment, wherein the server 1 may for example be placed at a central location in a hospital, and the infusion devices 3A, 3B may be placed on different wards in different rooms of the hospital.

The computing device 2 may be a portable device such that it for example can locally be connected to a particular medical device 3A, 3B.

In order to allow for a secure communication between the server 1 and the medical devices 3A, 3B, security keys in the shape of dedicated key pairs 4A, 4B are distributed from the server 1 via the computing device 2 to the different medical devices 3A, 3B. The key pairs 4A, 4B herein are generated at the server 1 and are stored in a security key database in a storage 10 of the server 1.

As indicated in FIG. 1, the server 1 generates, for each medical device 3A, 3B, a dedicated key pair 4A, 4B. Each key pair 4A, 4B comprises a server key and a device key, the server keys and the device keys being different between the different medical devices 3A, 3B.

In order to allow for a secure communication between the medical devices 3A, 3B and the server 1, the key pairs 4A, 4B generated at the server 1 must be distributed to the different medical devices 3A, 3B. This takes place via the computing device 2.

For distribution of the key pairs 4A, 4B, the computing device 2 establishes a communication link 11 with the server 1 and retrieves the key pairs 4A, 4B from the server 1. The computing device 2 is connected to the different medical devices 3A, 3B (at the same time or one after the other) via communication links 30A, 30B, which may for example be wired links such as serial links (e.g., RS 232 links). Via the local communication links 30A, 30B the key pairs 4A, 4B are sent to the medical devices 3A, 3B, such that a first medical device 3A receives a first key pair 4A, and a second medical device 3B receives a second key pair 4B and so on.

The distribution of the key pairs 4A, 4B from the server 1 to the medical devices 3A, 3B may take place via a security application running on the computing device 2. The security application can for example establish the communication link 11 to the server 1 and can transmit the received key pairs 4A, 4B to the medical devices 3A, 3B, without locally storing the key pairs 4A, 4B at the computing device 2. In this way it is made sure that the key pairs 4A, 4B do not become publicly known if for example the computing device 2 is lost or is attacked from the outside.

The server 1 may be set up such that only a specific security application running on a computing device 2 may receive the key pairs 4A, 4B. The key pairs 4A, 4B hence cannot be accessed by another device or another application from the outside.

The key pairs 4A, 4B are sent from the server 1 to the computing device 2 via a secured link making use of cryptographic algorithms, such as an asymmetric cryptographic algorithm, e.g. public key methods such as Transport Level Security (TLS) or PGP. Hence, the communication between the server 1 and the computing device 2 is protected.

Because the computing device 2 is locally connected via for example a wired link 30A, 30B to the medical devices 3A, 3B, the key pairs 4A, 4B can be send by the computing device 2 to the medical devices 3A, 3B in clear messages without using encryption. The medical devices 3A, 3B hence do not require substantial computational power and do not need to run complex cryptographic algorithms.

Upon distribution of the key pairs 4A, 4B, the communication between a medical device 3A, 3B and the server 1, for example for configuration of the medical device 3A, 3B or during operation of the medical device 3A, 3B, may take place in a secure fashion.

In particular, as illustrated in FIG. 2, a medical device 3A may send data in a clear message (for example within an HTTP session) comprising a signature generated according to the key pair 4A associated with the medical device 3A. The server 1 can read the signature and, according to the signature and the key pair 4A known to the server 1, can verify that the message has been sent by the medical device 3A (and not by another device) and has not been manipulated by another party. By means of the signature, hence, the medical device 3A is authenticated.

The signature may for example be generated by the medical device 3A using its device key. Upon receiving a message including the signature, the server 1 verifies the received signature according to the device key associated with the medical device 3A known to the server 1 by computing the signature and by comparing the computed signature to the received signature. Vice versa, the server 1 may send a clear message to the medical device 3A including a signature generated according to the server key, and the medical device 3A may verify the signature according to the server key known to the medical device 3A by computing the signature and comparing it to the received signature.

The message may include a timestamp or a counter and may hence have a non-static part. In this way it can be made sure that each message generated will have a different signature computed according to the key pair 4A. In particular, a message sent at a different time will have a different signature. In this way it can be made sure that a message replayed from a non-trusted third-party would have a non-matching signature, which can be detected by the server 1 respectively the medical device 3A.

Furthermore, as illustrated in FIG. 3, the medical device 3A may send an encrypted message (for example within an HTTPS session) being encrypted by the key pair 4A associated with the medical device 3A. The encrypted message is received by the server 1 and can be decrypted by the server 1 making use of the key pair 4A associated with the sending medical device 3A.

Again, the encryption done by the medical device 3A may make use of the device key associated with the medical device 3A. Upon receiving the encrypted message the server 1 can decrypt the message making use of the device key known to the server 1. Vice versa, the server 1 may send a message encrypted using the server key, and the medical device 3A may decrypt the received message using the server key known to the medical device 3A.

Again, a timestamp or counter may be included in the message such that the message contains a non-static part. Hence, a replay of the message from a non-trusted third-party is avoided, because in encryption of the message having another timestamp or another counter leads to a different encryption, which can be detected by the server 1 respectively the medical device 3A.

With the proposed scheme the distribution of the key pairs 4A, 4B from the server 1 to the medical devices 3A, 3B takes place in a secured fashion using highly secure cryptographic algorithms such as asymmetric key algorithms (public key cryptography), which generally are computationally expensive. This however does not pose a problem since the key distribution takes place via the computing device 2 running a security application. After key distribution, then, the further communication between the medical device 3A, 3B and the server 1, to exchange data between the medical device 3A, 3B and the server 1, may take place using the exchanged security key 4A, 4B. For this communication a symmetric key algorithm using a shared secret key may be used, which is computationally less expensive and hence does not pose a problem to a medical device 3A, 3B potentially having a reduced computing power.

The proposed scheme hence may make use of highly secure asymmetric key algorithms (public key algorithms) for the distribution of security keys. For the actual data exchange and communication, then, it may be made use of symmetric key algorithms (private key algorithms) which are computationally less expensive. Hence, the exchange of keys may make use of a different cryptographic algorithm than the later data communication.

Messages exchanged between a medical device 3A, 3B and the server 1 hence may be signed or encrypted using a secret key shared between the medical device 3A, 3B and the server 1. Each medical device 3A, 3B herein stores its secret key and the server key, and the server 1 stores the device key and its server key.

Each medical device 3A, 3B herein is associated with a dedicated key pair 4A, 4B having a specific device key and a specific server key. Because every medical device 3A, 3B is associated with a dedicated key pair 4A, 4B, a compromising of the server key in case of a device attack can be avoided.

The key pairs 4A, 4B may for example be distributed during the device configuration (via a security application running on the computing device 2).

Because the computing device 2 transfers the key pair 4A, 4B associated with a particular medical device 3A, 3B via a local link 30A, 30B, which in particular may be a wired link, for example a serial (RS232) link, to the particular medical device 3A, 3B, no particular encryption needs to be used for transferring the key pair 4A, 4B from the computing device 2 to the specific medical device 3A, 3B. Hence, no computationally expensive cryptographic algorithm must run on the medical devices 3A, 3B for the sake of distributing the key pairs 4A, 4B.

Generally, the key pairs 4A, 4B generated by the server 1 should be compliant with signature and/or encryption algorithms such as, for example, the SHA-1, AES-128 or AES-256 algorithm.

The secret key pair 4A, 4B associated with each medical device 3A, 3B should be stored in the security server database of the storage 10 of the server 1 in encrypted form. For this, the server 1 should use an internal secret key to encrypt ("salt") all security data, in particular the key pairs 4A, 4B, in its database in the storage 10.

The server 1 should support a signature and/or encryption algorithm compliant with the signature and/or encryption algorithm used by the medical device 3A, 3B, for example the SHA-1, AES-128 or AES-256 algorithm.

Encryption is not required on the most part of the use cases. It is recommended to use encryption only optionally on the side of the medical device 3A, 3B in order to save computational power and energy of the medical device 3A, 3B (which may for example run using a battery). Hence, it may be chosen on the side of the medical device 3A, 3B whether a message is sent using a signature created according to the key pair 4A, 4B associated with the medical device 3A, 3B, or whether a message is encrypted using a private key algorithm making use of the key pair 4A, 4B associated with the medical device 3A, 3B.

Generally, the key pair 4A, 4B associated with a medical device 3A, 3B should be exchanged and replaced by a new key pair 4A, 4B on a frequent basis. The frequency of key replacement herein may depend on a desired security level for the particular medical device 3A, 3B. The change of a key pair 4A, 4B may for example be triggered by the medical device 3A, 3B by sending a request message to the server 1. This message can be encrypted by using the old key pair 4A, 4B by the medical device 3A, 3B, and can be decrypted by the server 1 using the old key pair 4A, 4B known to the server 1. The server 1 may then respond by sending a message to the medical device 4A, 4B including a new key pair 4A, 4B, wherein this message again may be encrypted using the old key pair 4A, 4B and may be decrypted by the medical device 3A, 3B using the old key pair 4A, 4B. For future messages, then, the new key pair 4A, 4B is used.

The server 1 should be set up to be fully secure and protected against cyber-attack and local attack (similar to, e.g., a RADIUS (short for Remote Authentication Dial-In User Service) server in a public key infrastructure). All key pairs 4A, 4B should be stored in a secret key container in the database of storage 10, possibly storing a device unique identifier, the server key and the device key of each key pair 4A, 4B in cipher form.

The server 1 may, in one embodiment, use a public/private key pair to be used for example in an AES-256 algorithm to encrypt other data. Public/private key pairs should also be stored in the secret key container of the database of storage 10.

In the security application of the computing device 2, authentication may for example be managed using a trusted authentication system based on, e.g., a X.509 certificate. A certificate herein may be linked to a user to authenticate the user on the security application.

The security application of the computing device 2 may, in one embodiment, be set up to authenticate the server 1 (to avoid identity theft) and should be protected by requiring a user to provide a login name and a password (managed for example by a so-called Lightweight Directory Access Protocol (LDAP)). The security application should use an authentication involving a certificate (or any other authentication technology) to prove the user identity of the user logged on to the security application to the server 1.

The security application of the computing device 2, upon connection to the medical device 3A, 3B via a local link, for example an RS232 serial link, may be set up to retrieve a unique ID from the medical device 3A, 3B, and may be set up to send the unique ID to the server 1 in order to request a secret key pair 4A, 4B from the server 1. The security application herein may add information to the request.

Each time the security application requests a key pair 4A, 4B from the server 1, a new key pair 4A, 4B should be generated.

The medical device 3A, 3B may for example be an infusion device such as a syringe infusion pump or a volumetric (peristaltic) infusion pump. The medical device 3A, 3B should have a unique ID for its own authentication.

The medical device 3A, 3B should be able to receive secret keys from the security application of the computing device 2, which for example may be a laptop computer, a mobile device such as a smart phone or another computing device having sufficient computing power. The medical device 3A, 3B should store all secret key information received via the security application of the computing device 2 in a memory part protected against an external read operation. In particular, no maintenance or operating application of the medical device 3A, 3B should have access to the secret key information stored on the medical device 3A, 3B.

In case the distribution of a key pair 4A, 4B to a medical device 3A, 3B fails, or in case a problem with a key pair 4A, 4B arises, a new key pair 4A, 4B must be distributed to the medical device 3A, 3B. A restoration of a key pair 4A, 4B should be avoided.

The invention is not limited to the embodiments described above, but may be implemented in an entirely different fashion.

For example, a similar approach as the one described above for the distribution of key pairs for the communication between a medical device and a server may also be applied for configuring a medical device, for example an infusion device such as an infusion pump, to provide for a WiFi connectivity, for example for distributing a WPA2 password or a RADIUS Certificate to the medical device.

LIST OF REFERENCE NUMERALS

1 Security server
10 Storage
11 Link
2 Computing device (PC)
3A, 3B Medical device (infusion pump)
30A, 30B Link
31A Link
4A, 4B Key pair

The invention claimed is:

1. A method for key distribution between a server and a plurality of medical devices, each medical device of the plurality of medical devices comprising an infusion device, comprising:
providing, at the server, a plurality of security key pairs, each security key pair of the plurality of security key pairs to be used for a secure data communication with one of the plurality of medical devices, and each security key pair of the plurality of security key pairs comprising a server key and a device key,
establishing a first communication link between the server and a computing device,
establishing a second communication link between the computing device and each one of the plurality of medical devices,
retrieving, by the computing device, the plurality of security key pairs from the server via the first communication link, and
transmitting, by the computing device, one of the retrieved plurality of security key pairs to each one of the plurality of medical devices via the second communication link, wherein the retrieved plurality of security key pairs are not stored by the computing device, but are only transmitted to the plurality of medical devices.

2. The method according to claim 1, wherein the first communication link is an Internet Protocol link.

3. The method according to claim 1, wherein the first communication link uses an HTTPS session.

4. The method according to claim 1, wherein the second communication link is a wired link.

5. The method according to claim 1, wherein the second communication link is a serial connection.

6. The method according to claim 1, wherein the server generates a plurality of different, dedicated security key pairs, each security key pair of the plurality of different, dedicated security key pairs associated with one of the plurality of medical devices, and each security key pair of the plurality of different, dedicated security key pairs comprising a dedicated server key and a dedicated device key.

7. The method according to claim 6, wherein, for each particular medical device of the plurality of medical devices, the associated dedicated security key pair is retrieved from the server by the computing device and is transmitted to the particular medical device.

8. The method according to claim 1, wherein, upon distribution of a particular security key pair of the plurality of security key pairs, a third communication link is established between a particular medical device of the plurality of medical devices and the server to transmit messages in between the particular medical device and the server.

9. The method according to claim 8, wherein a message comprises a signature generated using at least one of the device key and the server key of the particular security key pair associated with the particular medical device and the server.

10. The method according to claim 8, wherein a message is encrypted using at least one of the device key and the server key of the particular security key pair.

11. The method according to claim 1, wherein a particular one of the plurality of medical devices requests, after initial transmission of a retrieved security key pair, a new security key pair by sending a message to the server, and the server sends the new security key pair in an encrypted message to the particular one of the plurality of medical devices.

12. A system for key distribution between a server and a plurality of medical devices, wherein each of the plurality of medical devices comprises an infusion device, the system comprising:
the server configured to provide a plurality of security key pairs, each security key pair of the plurality of security key pairs to be used for a secure data communication with one of the plurality of medical devices, and each security key pair of the plurality of security key pairs comprising a server key and a device key,
a computing device, wherein the server and the computing device are configured to establish a first communication link between the server and the computing device,
the plurality of medical devices, wherein the computing device and each one of the plurality of medical devices are configured to establish a second communication link between the computing device and the each one of the plurality of medical devices,
wherein the computing device is configured to retrieve the plurality of security key pairs from the server via the first communication link and to transmit one of the retrieved plurality of security key pairs to each one of the plurality of medical devices via the second communication link, the computing device being configured not to store the retrieved plurality of security key pairs, but to only transmit the retrieved plurality of security key pairs to the plurality of the medical devices.

* * * * *